United States Patent [19]

Cannon, III

[11] 4,102,345

[45] Jul. 25, 1978

[54] PACER DEMAND-RATE TEST MODE CONTROL

[75] Inventor: Robert Lee Cannon, III, Waltham, Mass.

[73] Assignee: American Optical Corporation, Southbridge, Mass.

[21] Appl. No.: 789,489

[22] Filed: Apr. 21, 1977

[51] Int. Cl.² .............................................. A61N 1/36
[52] U.S. Cl. .............................................. 128/419 PT
[58] Field of Search .................. 128/419 PG, 419 PT

[56] References Cited

U.S. PATENT DOCUMENTS

| | | | |
|---|---|---|---|
| 3,651,799 | 3/1972 | Daynard | 128/419 PG |
| 3,661,152 | 5/1972 | Berkovits | 128/419 PG |
| 3,662,759 | 5/1972 | Dabolt | 128/419 PG |
| 3,837,348 | 9/1974 | Thaler | 128/419 PT |

*Primary Examiner*—William E. Kamm

*Attorney, Agent, or Firm*—Jeremiah J. Duggan; Stephen A. Schneeberger

[57] ABSTRACT

In an implanted heart stimulating device of the demand type, test mode circuitry is arranged to cause the temporary generation of stimulation impulses at the demand-rate in the presence of naturally occurring heartbeats. The test mode circuitry may cause dependence of the heart-stimulation rate upon the level of the power source within the test mode or at least a portion of the test mode, but is arranged to provide a heart-stimulation rate independent of the level of the power source in the ordinary demand mode. The test mode circuitry is operative, through a relatively simple bias-modifying circuit, to force the pacer to generate at least several stimulating impulses at the demand-rate immediately following cessation of that portion of the test mode in which stimulation impulses are generated at a rate dependent upon the level of the power source. Subsequently, the pacer reverts to the ordinary (i.e., non-forced) demand mode.

10 Claims, 2 Drawing Figures

PACER DEMAND-RATE TEST MODE CONTROL

BACKGROUND OF THE INVENTION

1. Field of the Invention

This invention relates in general to implantable heart-stimulating devices. More particularly, the invention relates to external control over such devices for providing stimulating impulses at a so-called demand-rate, even in the presence of natural heartbeats. More particularly still, the invention relates to the provision of such test modes in such devices to allow at least the determination of the condition (i.e. remaining life) of the implanted power source.

2. Description Of Prior Art

Implantable heart-stimulating devices, of both a continuous and demand type, have been disclosed in prior art. External means for controlling operation of the implanted device has also been disclosed, i.e., externally magnetically operated reed switch. An example of these reed switches can be seen in U.S. Pat. No. 3,311,111 to Bowers. However, the operation of these prior art reed switches do not provide the test mode or modes of the present invention.

In another patent to Bowers, U.S. Pat. No. 3,563,247, there is disclosed an external control for varying rate of stimulation pulses. The patent discloses a variation in pulse rate for the purpose of stimulating the patient at a therapeutic rate different from the initial pacer rate provided. Although the present invention also provides a variation in pulse rate, it is not for providing the patient with a new therapeutic stimulation rate different from the initial pacer rate. The present invention utilizes rate information during a temporary test mode of operation to provide at least an indication of remaining life of the implanted power source. This is not disclosed in the prior art.

Certain pacers on the market today are designed to maintain a stable pulse rate regardless of battery condition. There is no apparent rate change or other indication of forthcoming failure of the device until several cells of the total number of cells have failed. Then catastrophic failure may occur. Although apparent life of the pacer is lengthened, actual life of the pacer is not changed at all.

This approach to implantable pacers is desirable from a marketing point of view, but undesirable from a life-support point of view. The patient's life depends on continued proper functioning of implanted circuitry. The pacer may lose capture (the ability of the pacer to stimulate the heart) because of the reduced pulse energy. With this type of design, there is no readily available way of checking the batteries at various times throughout the pacer's life.

It is thus desirable to know how much battery life remains at varying points in time after implantation. An undesirable way to determine battery life is to utilize a surgical procedure and remove the implanted pacer to test the batteries. This is, of course, a poor approach. It is desirable to make the determination of remaining power source life by observing some characteristic of the pacer while it remains implanted. This characteristic of the pacer should be selected to provide an indication to the observer of the state of the power source. A solution to this battery depletion-sensing problem is provided by utilizing an externally manually controlled test rate mode of operation. In the normal demans mode of operation, the pacer provides a pulse rate substantially independent of power source level.

A pacer having the immediately aforementioned externally manually controlled test rate mode of operation is disclosed in U.S. Pat. No. 3,774,619 to Goldberg. In that patent, an externally located and operated magnetic-field source was utilized to control implanted test mode pacer circuitry arranged to cause dependence of the heart-stimulation rate upon the level of the power source when in the test mode, but arranged to provide a heart-stimulating rate independent of the level of the power source when in the ordinary demand mode. The test mode circuitry included a magnetically operated reed switch, and other circuitry to cause a battery-dependent disproportionate change between the timing-capacitor charging rate and the threshold level of an implanted relaxation oscillator. This made the oscillator frequency and thus the heart-stimulating rate controllably dependent upon power source level.

In order to determine the condition (i.e. the level of depletion or remaining life) of the pacer's batteries, the stimulation rate occurring during the test mode and dependent upon the level of the power source required comparison with a stimulation rate which was independent of the remaining life of the batteries. Although the stimulating impulses occurring at the demand-rate would provide such reference for comparison, those stimulation impulses would not be present if the patient's heart was functioning normally. Accordingly, the 3,774,619 patent discloses using the so-called "interference-continuous" mode for obtaining stimulating impulses which occur at a rate relatively independent of the remaining life of the battery and subsequently subtracting some predetermined number of beats per minute from that rate to obtain the demand rate. While that technique for "computing" the demand-rate is generally satisfactory in instances where the demand-rate is not available, the rate associated with the "interference-continuous" mode may tend to vary somewhat, whereas the demand-rate is inclined to be more stable. Further, in order to create the "interference-continuous" mode of operation, it is necessary that the magnetic field which actuates the reed switch be pulsed at a rate of more than about 15 pulses per second, thereby obviously requiring an external oscillator.

Accordingly, it is a principal object of the present invention to provide an improved implantable heart-stimulating device of the demand type.

It is a further object of the invention to provide an implantable demand heart pacer capable of temporarily generating stimulating impulses at the demand-rate in the presence of natural (spontaneous) heartbeats.

It is an additional object of the invention to provide improved externally controlled implantable test mode circuitry to externally determine depletion of implanted batteries of a demand pacer.

These and other objects will be in part obvious and in part pointed out in greater detail hereinafter.

SUMMARY OF THE INVENTION

The invention comprises implanted test mode circuitry arranged to cause the temporary generation of stimulation impulses at the demand-rate in the presence of naturally occurring heartbeats. The test mode circuitry is further arranged, in a preferred embodiment, to cause dependence of the heart-stimulation rate upon the level of the power source within the test mode or at least a portion of the test mode, but is arranged to provide a heart-stimulation rate independent of the level of the power source in the ordinary demand mode. The test mode circuitry is operative to force the pacer to generate at least several stimulating impulses at the demand-rate immediately following cessation of that portion of the test mode in which stimulation impulses are generated at a rate dependent upon the level of the power source. Subsequently, the pacer reverts to the ordinary (i.e. non-forced) demand mode. It will be appreciated that other rate characteristics e.g., declining demand rate with a stable test rate, may be employed.

The advantage of the present invention is the provision of information regarding the state of the pacer circuitry and the implanted batteries without resorting to a surgical procedure to determine same.

DESCRIPTION OF THE PREFERRED EMBODIMENT

Figure 1:
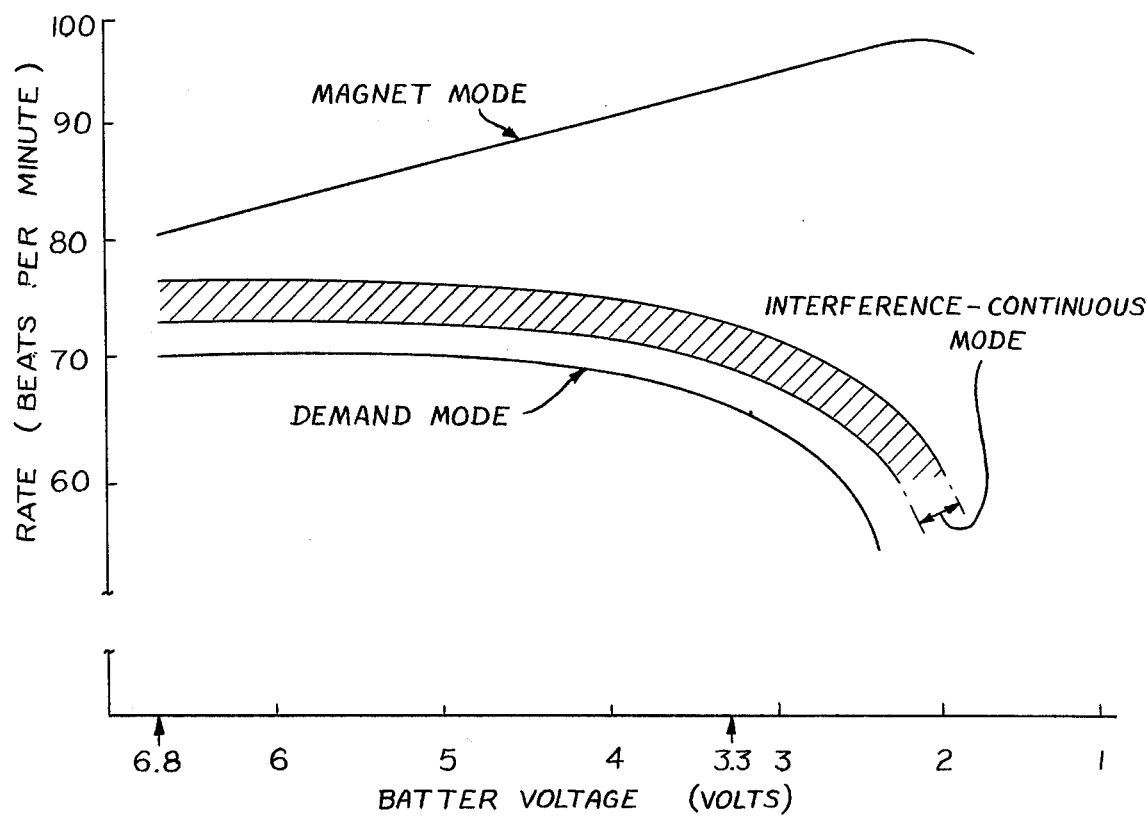
FIG. 1 is a graphical representation of rate characteristics of the pacer as a function of diminishing battery voltage.
Figure 2:
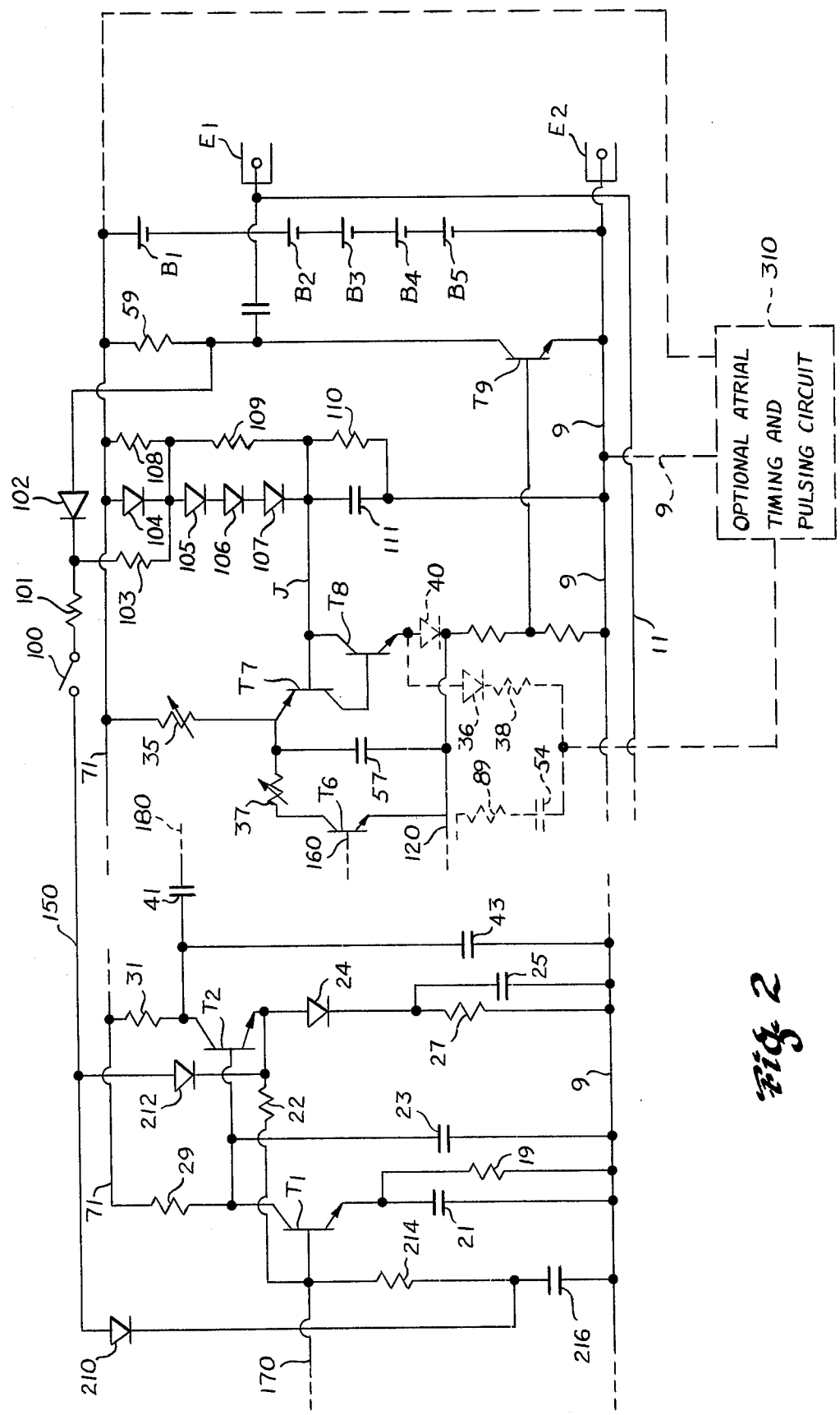
FIG. 2 is a schematic representation of an illustrative embodiment of the present invention.

FIG. 2 is a schematic of an illustrative embodiment of the present invention. The schematic of FIG. 2 is to be viesed in conjunction with FIG. 2 of U.S. Pat. No. 3,774,619 to Goldberg and additionally in conjunction with FIG. 1 of U.S. Pat. No. 3,757,791 to Berkovits. Generally speaking, the pacer circuitry illustrated in the right-half of the present FIG. 2 corresponds with the circuitry illustrated in FIG. 2 of U.S. Pat. No. 3,774,619 and the circuitry appearing in the left-half of the present FIG. 2 corresponds with the circuitry appearing in the left-half of FIG. 1 of U.S. Pat. No. 3,757,791. The relaxation oscillator comprised of transistors T6, T7, and T8 and timing capacitor 57 is common to the circuits of both aforementioned U.S. patents and may serve as a convenient reference point. The only circuit elements added by the present invention and not appearing in one or the other, or both, of the aforementioned U.S. patents are isolation diodes 210 and 212 and the bias-modifying R-C circuit comprised of resistor 214 and capacitor 216. The subject matter of the aforementioned patents is incorporated herein by reference to the extent consistent herewith. It will be appreciated that the heartbeat detection circuitry appearing in the left-half of the present FIG. 2 is also generally similar to that of U.S. Pat. No. 3,528,428 to Berkovits, with slight improvements thereto.

The illustrative embodiment is disclosed as being of the type which provides stimulation impulses to the ventricle of a patient's heart; however, it will be appreciated that the novel circuitry of the present invention is similarly applicable to a pacer of the type which provides stimulation impulses to the atrium and to the ventricle of the heart respectively. In this regard, the atrial timing and pulsing circuitry of the aforementioned U.S. Pat. No. 3,757,791 is illustrated in dotted line and represented by block 310 as an optional adjunct to the basic circuit. The dotted line elements including diodes 36 and 40, resistors 38 and 89, and capacitor 54 appearing in U.S. Pat. Nos. 3,757,791 would be utilized if the particular pacer was to have an atrial-ventricular stimulation capability.

With reference to FIG. 2, showing component interconnection, the anode of diode 102 is connected to the junction of resistor 59, and capacitor 65. The cathode of diode 102 is connected to the junction of resistors 101 and 103. The other end of resistor 101 is connected to one end of an externally operated implantable magnetic reed switch 100. The other end of reed switch 100, the fixed end, goes to conductor 150.

The other end of resistor 103 is connected to a junction comprised of a cathode of diode 104, the anode of diode 105, and resistors 108 and 109. Diodes 104 and resistor 108 are in parallel connection. Diodes 105, 106 and 107 are in series string and are in a parallel connection with resistor 109. The junction of resistor 109 and the cathode of diode 107 are connected to one end of parallel combination of capacitor 111 and resistor 110, the other end of which parallel combination is connected to conductor 9. The junction of resistors 109 and 110 (junction J) is connected to the base of transistor T7. The potential at this junction is the threshold level for the timing circuitry, and will be discussed below in detail.

Now, interrelating the circuitry of the instant application with U.S. Pat. No. 3,757,791, conductor 150 is connected through isolating diode 212 to the emitter of transistor T2 in FIG. 1 of this patent. Conductor 160 is connected to the junction of capacitor 54 and resistor 55 in this patent. Conductor 120 is connected to the other end of resistor 55 in this patent. Conductor 170 is connected to that end of capacitor 20 which is electrically in common with resistor 22 in this patent. For additional reference, conductor 9 is connected to the reference end of resistor 15 and signal conductor 11 is connected to the input side of capacitor 17, capacitors 17 and 20 and shunt resistor 15 (all not shown) providing a frequency selective input to transistor T1. Conductor 71, in the present instance, also corresponds with conductor 140 of U.S. Pat. No. 3,774,619. In this illustrative embodiment of the present invention, switch S of FIG. 1 of U.S. Pat. No. 3,757,791 is omitted (i.e. consider switch S to be held open at all times). Conductor 180, connected to one end of capacitor 41 in U.S. Pat. No. 3,757,791, is connected to the junction of resistors 26 and 30 and the anode of diode 28 therein (none of which are shown).

In operation, first consider the situation with switch 100 open as is shown. Current from the series string of batteries B1-B5 flows through resistor 59 and charges up capacitor 65 which holds the voltage as long as transistor T9 is not turned on. Current from the series string of batteries also flows through the parallel combination of diode 104 and resistor 108; the individual currents of that parallel branch combine to flow almost exclusively through resistor 109.

Diodes 105, 106 and 107 although in parallel with resistor 109, conduct negligible current in this "static" situation. Resistor values of resistors 108, 109 and 110, which form a voltage divider, are chosen to keep voltage across diodes 105, 106 and 107 below their combined forward voltage drop. This voltage is sufficiently low to prevent the diodes from conducting significantly in a forward direction. Diodes 105, 106 and 107 conduct significant current only during initial turn on of the circuitry when the batteries are initially connected. The diodes are used to counteract adverse transients during turn on. However, after a steady state situation is established, these diodes are functionally out of the circuit. They can be ignored without sacrificing any understanding of the operation of the instant invention.

With switch 100 open, as shown, normal demand mode of operation is permitted. If the heart demands a stimulating impulse, transistors T7 and T8 cause T9 to conduct, causing capacitor 65 to discharge through electrodes E1, E2, and the heart (not shown). In order to cause this stimulation, the potential on the emitter of T7 must exceed the potential on its base. This is described in the U.S. Pat. No. 3,757,791 in detail.

When T8 conducts, some of the current for the collector of T8 comes from the charged up capacitor 111. After T8 stops conducting, capacitor 111 recharges to its former state through resistors 108 and 109. Capacitor 111 is chosen so that it does not recharge to its previous static voltage value in a time equal to or less than the time between pulses of an ordinary heart rate. Thus, when a second stimulation pulse is demanded after the first stimulation pulse, capacitor 111 has not charged up to its previous static state. Thus, voltage at junction J is slightly lower than it previously was. Threshold J is overcome by voltage at the emitter of transistor T7 earlier than it was for the first stimulation pulse. Voltage on capacitor 111 charges and discharges in this manner and thus "ripples" while successive stimulation pulses are being generated. Successive stimulation pulses are separated from each other by respective time intervals that are each less than that time interval between the last natural heartbeat and the first stimulation pulse. This is known in the art as rate hysteresis and is not the subject matter of the present invention but is presented for purposes of completeness.

Bearing in mind that switch 100 is open, consider the function of diode 104. Diode 104 is a compensating diode which compensates for the non-linear base-emitted voltage drop of transistor T7. When the batteries are fully charged and operating, component values for resistors 108, 109 and 110 are selected so that current drawn from these batteries is shared by resistor 108 and diode 104. The diode current could be approximately 0.5 microamps; it is sufficient current through diode 104 to provide compensation for the base-emitter junction of transistor T7 when the batteries start to diminish in voltage. (The base-emitter junction is essentially a diode also).

For example, consider one of the batteries B1-B5 to fail. The current through diode 104 is diminished somewhat in accordance with constraints imposed by voltage divider action of resistor 108 in combination with resistors 109 and 110. (Recall that diodes 105, 106 and 107 are functional out of the circuit.) The decrease in supply voltage is felt by timing capacitor 57 which charges towards a lower voltage, and is also felt at junction J. It is the compensating effect of diode 104 which allows junction J to decrease in voltage in a manner (with respect to decrease of charging rate of capacitor 57) so as to hold the demand rate approximately constant. Thus, decreased overall supply voltage will not substantially change the stimulation rate of the pacer. This is depicted in FIG. 1. The demand mode rate is shown to be approximately flat for maximum battery voltage to approximately 4 volts. In a particular case this corresponds to the failure of two cells.

By contrast, if diode 104 did not exist (was open) junction J would decrease in proportion to the decrease of supply voltage in a linear fashion because of pure resistive voltage divider action. But, the base-emitter voltage drop of transistor T7 is a relatively fixed amount which is added to the linearly decreased voltage at threshold J to arrive at that voltage to which capacitor 57 must charge prior to generating a stimulating impulse to the heart. Thus, if diode 104 were open or were missing, the rate versus battery voltage characteristic of FIG. 1 would not be relatively flat.

By comparison consider a magnet mode or test mode. Switch 100 is a magnetically operable reed switch and is closed in response to effects of an external magnet (not shown). Current flows through diode 104, resistor 103, resistor 101 diode 212 and resistor 27 to ground. Current through diode 104 when switch 100 is closed is approximately 10 times the amount of current through diode 104 when switch 100 is open. Other current differentials can be used besides the factor of approximately 10. The increased current through diode 104 causes its voltage drop to substantially increase. This, in turn, causes the potential at threshold J to be decreased from total battery by an equal amount. The decrease in potential at junction J accounts for part of the marked increase in heart stimulation rate from the demand mode curve to the magnet mode curve as depicted in FIG. 1. (The reason for the other part of the increase is described below.) The decreased threshold voltage at J enables capacitor 57 to charge to that decreased threshold level more rapidly providing the increased rate.

Now, consider a failure of one or two batteries with switch 100 remaining closed. The total battery voltage supplied is reduced by about 20-40 percent. Current flow through diode 104 does decrease but due to the nonlinearity of diode 104, its forward voltage drop remains approximately constant. Thus, voltage change at threshold J is a greater percentage decrease than total battery voltage percentage decrease. In other words, threshold J voltage decreases proportionately faster than the total battery voltage decreases. At the same time, the voltage towards which capacitor 57 is charging decreases linearly with total battery voltage. As capacitor 57 charges under these conditions T7 is turned on earlier. As shown in FIG. 1, the rate of stimulation increases with decreasing total battery voltage. One can measure stimulation rate in the magnet mode and (from curves similar to those in FIG. 1) determine to what extent the batteries have become depleted and/or have failed.

Closure of switch 100 also causes other functionings. For example, the pacer is caused to be in a continuous stimulation test mode. This is accomplished by causing transistor T2 to cut off or be clamped (and not detect any heartbeats) because of a voltage impressed at the emitter of T2 through resistor 59, diode 102, resistor 101 and diode 212. It will be appreciated that other means for disabling T2, or for that matter T1 or related circuitry, such as by opening a circuit, would also cause the pacer to operate in the continuous mode. Continuous stimulation is preferred when testing battery level; otherwise, if the patient's heart were functioning normally and no pacer-generated stimuli appear, then, usually no measurements may be taken.

However, the aforementioned disabling of transistor T1 in the magnet mode prevents transistor T6 from conducting in response to a heartbeat (either natural or stimulated). The collector to emitter drop of transistor T6 is approximately 0.1 volts. The double base-emitter junction drop of transistors T7 and T8 is approximately 0.5 volts. Thus, in the mode where switch 100 is closed, capacitor 57 is caused to recharge from a higher voltage pedestal (0.5 volts vs. 0.1 volts). This pedestal effect in itself will permit capacitor 57 to charge to trigger voltage in a shorter time than when switch 100 is open. This accounts for the other part of the rate increase between the demand mode curve and the magnet mode curve of FIG. 1.

Therefore, closure of switch 100 in this phase of the magnet mode causes (1) rate of stimulation pulses to be increased and to increase as a function of diminishing battery voltage, and (2) the pacer to stimulate continuously. These functions occur simultaneously.

At this juncture, it is appropriate to consider in somewhat greater detail the circuitry involved in the detection of the patient's heartbeat (i.e. QRS complex) and/or a particular stimulating impulse from the pacer. In accordance with conventional prior art circuitry as disclosed in the aforementioned U.S. Pat. No. 3,757,791, normally only signals having frequencies commensurate with the QRS complex and above are detected. Transistor T1 is normally conducting, the emitter terminal of the transistor being connected through resistor 19 and conductor 9 to the negative terminal of battery 1, and the base of the transistor being connected through resistor 22 to a more positive potential at the emitter of transistor T2. The electrical signals picked up by the electrodes implanted in the patient's heart are coupled across capacitor 17 and resistor 15 in the base circuit of transistor T1. Signals of either polarity are amplified by transistor T1. The transistor is biased for class A operation because the polarity of the detected signal may be of either type depending on the manner in which the electrodes are implanted. Resistor 19 and capacitor 21 in the emitter circuit of transistor T1 serve to decrease the overall gain of the transistor as the frequency decreases.

The amplified signal at the collector of transistor T1 is applied across the base-emitter junction of transistor T2, this transistor also being biased for class A operation. Transistor T2 further amplifies the detected signals. Capacitor 25 and resistor 27 in the emitter circuit of transistor T2 serve the same function as resistor 19 and capacitor 21 in the emitter circuit of transistor T1. This high-pass filter further limits the low frequency response of the detecting circuit to discriminate against the P and T waves and any other frequencies well below 20 Hz. Resistor 29 and capacitor 23 as well as resistor 31 and capacitor 43 serve as an integrator to reduce the effects of small signal-high frequency noise components well above 30 Hz. It should be noted, however, as will be hereinafter discussed in greater detail, that the attenuating effects are only proportional to the magnitude of the input signal such that large magnitude-high frequency signals may be significantly retained.

Transistor T2 functions primarily as an amplifying stage. However, it also serves to provide a biasing potential for transistor T1. However, in such a case it is necessary to derive an intermediate positive potential to bias the base of transistor T1 for class A operation. This is accomplished by connecting resistor 22 between the emitter of transistor T2 and the base of transistor T1. The positive potential at the emitter of transistor T2 (equal to the voltage drop across diode 24 and resistor 27) is extended through resistor 22 to bias transistor T1 for class A operation. This DC feedback eliminates the need for a battery tap. Diode 24 serves simply as a level-shifting diode - it increases the potential at the emitter of transistor T2 by the drop across it without affecting the AC gain of the stage.

The AC signals on the collector of transistor T2 are coupled through capacitor 41 to additional circuitry generally characterized as rate-discrimination circuitry.

(In order to avoid unnecessary repetition, certain components having the following reference designations are shown in U.S. Pat. No. 3,757,791 and are not shown in FIG. 2 of the present application: resistors 45, 34 and 47, and capacitors 49 and 53.) The AC signal from transistor T2 will normally take the form of a pulse which is ultimately applied as a current pulse to the capacitor 49. This current pulse is normally of sufficient magnitude to fully charge capacitor 49. Resistors 34 and 47 are connected in parallel with capacitor 49 and serve to provide a controlled rate of discharge. Under normal conditions, the capacitor 49 nearly or fully discharges between successive heartbeats. Accordingly, each successive current pulse applied to capacitor 49 operates to recharge it to the maximum voltage. The potential across capacitor 49 during recharge is AC-coupled through capacitor 53 to the base of transistor T6 to effect its turn on said resulting discharge of timing capacitor 57.

On the other hand, the values of resistors 34 and 47 are selected such that if input current pulses recur at a relatively high rate (i.e. 40 per second or greater) due to interference, and from a 60 Hz source, the capacitor 49 will not significantly discharge between successive input current pulses. Accordingly, the potential across capacitor 49 for each successive high-rate input pulse is relatively small and is ineffective to cause conduction of transistor T6 and the discharge capacitor 57.

This latter situation is termed the interference-continuous mode of operation in which high repetition rate input signals effectively serve to disable transistor switch T6, thereby forcing capacitor 57 to discharge through T6 and T8 such that the pacer stimulation rate is continuous and at a somewhat higher rate than the normal demand rate.

For purposes of the present invention, it is important to note that although short-duration signals of relatively low magnitude (i.e. atrial stimulating pulse) are not of sufficiently long duration to significantly charge capacitor 49 and thereby drive T6 into conduction, similar short-duration pulses of much greater magnitude have the effect of creating a response by transistors T1 and T2 which is similar to that evoked by a QRS complex. Although the amplifiers including transistors T1 and T2 include some degree of high frequency rejection circuitry, they are relatively easily overloaded by the relatively large voltage signal of the ventricular stimulating impulse sensed at the base of transistor T1 such as to result in a mid-band response akin to that from the QRS complex.

As previously mentioned, the "interference-continuous" mode of operation results in a stimulation rate by the pacer which is slightly faster than that of the normal demand-rate. In those instances in which the patient's heart is beating normally and the demand-rate has not been available from the pacer, it has been the practice to use this "interference-continuous" rate for the purpose of mathematically determining the demand-rate against which the "magnet mode" rate was then compared to provide a measure of remaining battery life. However, the stimulation rate associated with the "interference-continuous" mode is capable of significant rate variation at any particular battery voltage for a particular pacer, as illustrated in FIG. 1. Therefore, the "interference-continuous" rate is less than ideal for the subsequent determination of demand-rate and ultimately, the remaining battery life. Additionally, the "interference-continuous" mode is realizable only through the use of an external oscillator capable of switching the magnetic field, and thus switch 100, on and off at a rate sufficiently fast to simulate interference.

In accordance with the invention, additional circuitry is utilized in conjunction with and as a second or follow-up phase to the magnet mode for the purpose of "forcing" the generation of stimulating impulses at the demand-rate even though the patient's heart is spontaneously or naturally heating. In addition to the circuitry previously described, and the connection of the source voltage to the emitter of T2 via switch 100 and diode 212, this desired result is obtained simply through the addition of a bias-modifying circuit comprised of resistor 214 and capacitor 216 connected with the source voltage through reed switch 100 and isolating diode 210.

The resistor 214 and capacitor 216 are connected in series with one another and in parallel with the base-emitter circuit of T1. More specifically, one end of resistor 214 is connected to the base of T1 with the other end thereof being connected to one end of capacitor 216, the other end of capacitor 216 being connected to the reference conductor 9. An isolating diode 210 having its cathode connected to the junction between resistor 214 and capacitor 216 and having its anode connected to conductor 150 serves in combination with isolating diode 212, to isolate the R-C network 214, 216 from the emitter circuit of transistor T2.

Under normal operating conditions, the R-C network 214, 216 does not significantly enter into the operation of the pacer as heretofore described and the capacitor 216 is only slightly charged above the potential of conductor 9. However, when switch 100 is closed by the application of an external magnetic field, the capacitor 216 charges to a significantly higher voltage level determined by the voltage-divider action of series resistors 59, 101, and 27. The resistances of resistors 59 and 101 are sufficiently smaller than that of resistor 27 such that the voltage to which capacitor 216 charges may be a significant percentage (i.e. 25–50% or more) of the power source itself with switch 100 closed. The level to which capacitor 216 charges with switch 100 closed is sufficient to insure, when the switch is opened following the removal of the external magnetic field, that the bias voltage applied to the base of transistor T1 by capacitor 216 through resistor 214 is such that the relatively small magnigutde QRS complex signals of a natural heatbeat (regardless of polarity) are not detected and amplified by the transistor. On the other hand, this modification of the bias applied to the base of transistor T1 is not so great as to prevent the ventricular stimulating impulses appearing on conductor 170 from being detected and amplified by transistor T1 and, accordingly, transistor T2 and the subsequent circuitry. As previously noted, the ventricular stimulating impulse is of considerably greater magnitude than the QRS complex of the natural heartbeat and of significantly greater magnitude than even an atrial stimulating impulse, should the pacer be of the atrial-ventricular stimulating type. This latter situation arises because the sensing electrode E1 is positioned in the ventricle relatively remote from the origin of any atrial stimulating pulse.

Although the charge stored on capacitor 216 begins to decay through resistor 214 when switch 100 is opened, their respective values are selected to have a time constant which ensures that this modified bias applied to transistor T1 remains above that level necessary to exclude detection of QRS complexes for at least several seconds, thereby ensuring the generation of several stimulating pulses at the demand-rate as will be hereinafter described.

For that interval of several seconds or more following the opening of switch 100 and during which the bias on the base of transistor T1 remains above that level required to prevent detection of the QRS complexes, only the ventricular stimulating impulses will be detected and passed by the transistor amplifiers T1 and T2. Although of short duration, the stimulating pulse signals are of such large magnitude as to override or overload the high frequency-limiting aspects of the amplifier circuits and produce current pulses for connection to capacitor 49 similar to those produced by a normal QRS complex. As earlier described, such pulses are ultimately connected to the base of T6 for effecting the maximum discharge of capacitor 57 and thereby ensuring operation at the demand-rate. When the charge level on capacitor 16 has finally decayed to a level at which the bias on transistor T1 again enables recognition of the QRS complex, the pacer will revert to a "non-forced" demand mode in which stimulating pulses are generated only if the patient's heart is not beating naturally.

Even if the frequency response characteristics of the signal detection amplifiers possess wider-band characteristics such that the current pulse delivered to capacitor 49 was indeed of very limited (i.e. 2 milliseconds) duration, the so-called "pacer tail" or recharge waveform which follows the stimulating pulse is of sufficient magnitude (i.e. several hundred millivolts) and essentially the same frequency composition as the QRS complex as to evoke the necessary response earlier described.

The invention may be embodied in other specific forms without departing from the spirit or essential characteristics thereof. The present embodiments are, therefore, to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. In an improved implantable electronic demand heart pacer for providing stimulation to the heart of a patient, said pacer including terminal means for connection to said heart, a power source for energizing circuitry of said pacer, pulse generator means connected to said source for supplying heart-stimulating impulses at predetermined rates on said terminal means, means for detecting the beating action of said patient's heart as well as said stimulation impulses, means responsive to said detecting means for enabling said pulse generator means to supply said impulses at a demand-rate substantially only in the presence of detected stimulation impulses and the absence of detected heartbeats, and test mode means including manual means for making said stimulation rate dependent upon and indicative of the condition of said source, the improvement comprising:

said test mode means further including demand-rate control means operative for temporarily preventing detection of the patient's heartbeats by said detecting means while concurrently allowing said detecting means to detect said stimulation impulses whereby said means responsive to said detecting means enables said pulse generator to supply said stimulation impulses at said demand-rate in the presence of heartbeats.

2. The improvement of claim 1 wherein said manual means additionally comprises said demand-rate control means, said demand-rate control means being operative in timesequential relationship with said means for making said stimulation rate dependent upon the condition of said source.

3. The improvement of claim 2 wherein said means for preventing detection of the patient's heartbeat while allowing detection of said stimulation impulses is operative at least for an interval sufficient to provide plural stimulation pulses at said demand-rate.

4. The improvement of claim 3 wherein said interval of operativity is of at least several seconds duration.

5. The improvement of claim 2 wherein said detecting means comprises amplifying means, said amplifying means being biased to normally respond to the beating action of the patient's heart as well as to said stimulation impulses, and said demand-rate control means comprises means for temporarily modifying the bias to said amplifying means such that said amplifying means continues to respond to said stimulation pulses but does not respond to the patient's heartbeat.

6. The improvement of claim 5 wherein said demand-rate control means includes a resistance-capacitance circuit connected to the input of said amplifying means, the current to the input of said amplifying means from said resistance when said capacitance is charged about a particular level being sufficient to provide said modified bias to said amplifying means, and said manual means includes selectively actuable switch means for connecting said resistance-capacitance circuit with said source for charging said capacitance at least above said particular level, the time-constant of said resistance-capacitance circuit being such that the charge on said capacitance remains above said particular level for at least several seconds following actuation of said switch means to disconnect said resistance-capacitance from said source.

7. The improvement of claim 6 wherein said switch means is further operative to disable either said detecting means or said detecting means responsive means only during said connection of said resistance-capacitance circuit with said source thereby to concurrently prevent generation of said stimulation impulses at said demand-rate.

8. The improvement of claim 7 wherein said disabling means for either said detecting means or said detecting means responsive means comprises a clamping voltage from said source connected thereto by said switch means.

9. In an improved implantable electronic demand heart pacer for providing stimulation to the heart of a patient, said pacer including terminal means for connection to said heart, a power source for energizing circuitry of said pacer, pulse generator means connected to said source for supplying heart-stimulating impulses at predetermined rates on said terminal means, means for detecting the beating action of said patient's heart as well as said stimulation pulses, and means responsive to said detecting means for enabling said pulse generator means to supply said impulses at a demand-rate substantially only in the presence of detected stimulation impulses in the absence of detected heartbeats, the improvement comprising:

test mode means for temporarily preventing detection of the patient's heartbeats by said detecting means while concurrently allowing said detecting means to detect said stimulation impulses whereby said means responsive to said detecting means enables said pulse generator to supply said stimulation impulses at said demand-rate in the presence of heartbeats.

10. In an improved implantable electronic demand heart pacer for providing stimulation to the heart of a patient, said pacer including terminal means for connection to said heart, a power source for energizing circuitry of said pacer, pulse generator means connected to said source for supplying heart-stimulating impulses at predetermined rates on said terminal means, means for detecting the beating action of said patient's heart as well as said stimulation impulses, means responsive to said detecting means for enabling said pulse generator means to supply said impulses at a demand-rate substantially only in the presence of detected stimulation impulses and the absence of detected heartbeats, means for maintaining said demand stimulation rate substantially independent of remaining life of said source, and test mode means including manual means for disabling said maintaining means and for making said stimulation rate dependent upon and indicative of the condition of said source, the improvement comprising:

said test mode means further including demand-rate control means operative in time-sequential relationship with said disabling means for temporarily preventing detection of the patient's heartbeats by said detecting means while concurrently allowing said detecting means to detect said stimulation impulses whereby said means responsive to said detecting means enables said pulse generator to supply said stimulation impulses at said demand-rate in the presence of heartbeats.

* * * * *